(12) United States Patent
Nawa

(10) Patent No.: US 7,331,773 B2
(45) Date of Patent: Feb. 19, 2008

(54) PUMP PROVIDED WITH EXHAUST VALVE DEVICE AND HEMODYNAMOMETER INCORPORATING THE SAME

(75) Inventor: Ikuichiro Nawa, Kanagawa (JP)

(73) Assignee: Mitsumi Electric Co., Ltd., Tokyo (JP)

( * ) Notice: Subject to any disclaimer, the term of this patent is extended or adjusted under 35 U.S.C. 154(b) by 543 days.

(21) Appl. No.: 10/880,087

(22) Filed: Jun. 30, 2004

(65) Prior Publication Data

US 2005/0047934 A1    Mar. 3, 2005

(30) Foreign Application Priority Data

Aug. 29, 2003   (JP)   ............................ P2003-307993

(51) Int. Cl.
  F04B 45/00    (2006.01)
  F04B 45/047   (2006.01)
  F04B 45/04    (2006.01)
  A61B 5/022    (2006.01)

(52) U.S. Cl. .................. 417/440; 417/12; 417/26; 417/357; 417/366; 417/413.1; 417/531; 417/559; 417/565; 417/566; 600/498

(58) Field of Classification Search .................. 417/12, 417/26, 413.1, 510, 357, 366, 440, 531, 559, 417/565, 566; 600/498
See application file for complete search history.

(56) References Cited

U.S. PATENT DOCUMENTS

| 4,337,223 A | * | 6/1982 | Kaye ........................... 422/112 |
| 4,990,066 A | * | 2/1991 | Kern ........................... 417/307 |
| 5,220,925 A | * | 6/1993 | Hishida ....................... 600/493 |
| 5,556,073 A | * | 9/1996 | Wawro et al. ........... 251/129.11 |
| 6,592,339 B1 | * | 7/2003 | Fukushima et al. .......... 417/269 |

FOREIGN PATENT DOCUMENTS

| JP | 63-14809 | 4/1988 |
| JP | 2002-106471 | 4/2002 |

* cited by examiner

*Primary Examiner*—Devon C. Kramer
*Assistant Examiner*—Leonard J Weinstein
(74) *Attorney, Agent, or Firm*—Whitham Curtis Christofferson & Cook, P.C.

(57) ABSTRACT

A diaphragm is provided in a pump case so as to define a pump chamber communicated with an external member having an air chamber. A motor actuates the diaphragm to introduce air into the pump chamber and to supply the introduced air to the air chamber. An exhaust valve exhausts air in the pump chamber to lower a pressure in the air chamber. The exhaust valve is provided with a valve body and an actuator which is driven by the motor to actuate the valve body so as to open or close an exhaust port communicated with the pump chamber.

5 Claims, 5 Drawing Sheets

PUMP PROVIDED WITH EXHAUST VALVE DEVICE AND HEMODYNAMOMETER INCORPORATING THE SAME

BACKGROUND OF THE INVENTION

The present invention relates to a compact pump provided with an exhaust valve device and a hemodynamometer employing the compact pump. Specifically, the invention relates to a compact pump which supplies air to an air chamber such as a cuff of the hemodynamometer to raise the pressure in the air chamber, and then releases the air to lower the pressure in the air chamber.

Such a compact pump is incorporated in, for example, an oscillometric hemodynamometer. In the oscillometric hemodynamometer, a pump supplies air to a cuff wound around an upper arm of a patient to compress an artery at a predetermined pressure to temporarily block a blood stream, and the air is then released by a normal exhaust valve to gradually lower the pressure in the cuff. Incidentally, the variations of the internal pressure of the cuff and the vibration amplitude in accordance with the artery pulsations are processed by a microcomputer to measure the systolic blood pressure and the diastolic blood pressure. After the measurement processing, a rapid exhaust valve is operated to rapidly lower the internal pressure of the cuff.

Generally, it is preferable that the normal exhaust valve which is employed in the hemodynamometer has such a property that the pressure in the cuff is lowered at a constant speed of about 3 to 4 mmHg/sec., and the rapid exhaust valve has such a property that the pressure in the cuff is rapidly lowered.

FIG. 5 shows such a compact pump which is disclosed in Japanese Patent Publication No. 2002-106471A.

A compact pump 1 comprises: a pump body 2 which is driven by a motor (not shown); a normal exhaust valve 3 which exhausts an air through a slit at a constant speed (such an exhaust valve is disclosed in Japanese Utility Model Publication No. 63-14809Y, for example); a rapid exhaust valve 4 which is actuated by a plunger; and a flexible tube 5.

The normal exhaust valve 3 and the rapid exhaust valve 4 are separately provided from the pump body 2. The tube 5 interconnects an exhaust port 6 of the pump body 2, the normal exhaust valve 3 and the rapid exhaust valve 4, and is also connected to a cuff (not shown) which is wound around an upper arm of a patient. Inside the tube 5, there is formed an air passage 8 which communicates respectively with a pump chamber 7 in the pump body 2, the normal exhaust valve 3, the rapid exhaust valve 4, and the cuff.

With the above configuration, when the pump body 2 is driven, exterior air is introduced into the pump chamber 7 and is then supplied to the cuff from the exhaust port 6 via the air passage 8 formed in the tube 5. When the internal pressure of the cuff reaches a predetermined pressure, the normal exhaust valve 3 is activated to exhaust air in the air passage 8. Incidentally, a larger amount of air than the amount of the air exhausted by the normal exhaust valve 3 is introduced into the cuff from the pump chamber 7.

Here, since the driving of the pump body 2 is halted, the internal pressure of the cuff is gradually lowered by the normal exhaust valve 3. Incidentally, the variations of the internal pressure of the cuff and the vibration amplitude in accordance with the artery pulsations are processed by a microcomputer to measure the systolic blood pressure and the diastolic blood pressure. After the measurement processing, a rapid exhaust valve 4 is activated to rapidly lower the internal pressure of the cuff.

In the above configuration, since the normal exhaust valve 3 and the rapid exhaust valve 4 are separately provided from the pump body 2, a large number of the components are required, the structure becomes complicated, thereby increasing the manufacturing cost.

Moreover, a piping structure of the tube 5 (the air passage 8) becomes complicated. Since the tube 5 is exposed to the exterior of the pump body 2, the tube 5 might sometimes come into contact with other members and bent or crooked when the compact pump 1 is assembled, thereby lowering the workability of the assembling operation.

Further, a plunger for exclusive use is adopted as an actuator for the rapid exhaust valve 4, thereby increasing the component cost.

SUMMARY OF THE INVENTION

It is therefore an object of the invention to provide a pump provided with an exhaust valve device which is capable of decreasing the component cost, simplifying and downsizing the pump structure, and improving the facility to attach the pump to other equipment such as a hemodynamometer.

In order to achieve the above object, according to the invention, there is provided a pump, comprising:
a pump case;
a diaphragm, provided in the pump case so as to define a pump chamber communicated with an external member having an air chamber;
a motor, which actuates the diaphragm to introduce air into the pump chamber and to supply the introduced air to the air chamber; and
a rapid exhaust valve, which rapidly exhausts air in the pump chamber to lower a pressure in the air chamber, the rapid exhaust valve comprising:
a valve body; and
an actuator, which is driven by the motor to actuate the valve body so as to open or close a rapid exhaust port communicated with the pump chamber.

With this configuration, since the opening/closing operation of the rapid exhaust valve is performed with the aid of the driving force of the motor, it is possible to omit a large and heavy actuating component such as a plunger. Accordingly, the weight reduction and the downsizing of the pump can be attained.

Preferably, the actuator comprises: a first gear, coupled with a rotary shaft of the motor; a second gear, meshing with the first gear to be rotated; a lever member, pivotably provided about the rotary shaft; and a clutch mechanism, connecting the second gear and the lever member such that the lever member is pivoted in accordance with the rotation of the rotary shaft. The lever member is pivoted in such a direction that the second gear is abutted against the valve body so that the valve body is moved so as to open the exhaust port, when the rotary shaft is rotated in a first direction. The lever member is pivoted in such a direction that the second gear is separated from the valve body so that the valve body is moved so as to close the exhaust port, when the rotary shaft is rotated in a second direction.

In this case, since the opening/closing operation of the rapid exhaust valve can be controlled by the rotating direction of the motor, the switching operation of the rapid exhaust valve can be simplified Here, it is preferable that the motor is halted at a predetermined timing after the valve body opens the rapid exhaust port. The rapid exhaust valve further comprises: an urging member which urges the valve body toward a position for closing the rapid exhaust port; and a stopper against which the lever member is abutted with the aid of a force urging the valve body even when the motor is halted.

In this case, the needless power consumption and the overheat problem can be avoided.

It is further preferable that: the valve body is pivotably provided in the pump case; and the urging member urges the valve body such that the urging force is directed in a tangential direction of the pivotal movement of the valve body. In this case, the closing state of the rapid exhaust valve can be secured.

Preferably, at least a part of the valve body is monolithically formed with the diaphragm.

In this case, it is possible to decrease the components in number, simplification, donsizing and decrease in weight of the structure.

According to the invention, there is also provided a hemodynamometer, comprising:

a cuff, adapted to be attached on a patient body and having an air chamber; and a pump, comprising:
  a pump case;
  a diaphragm, provided in the pump case so as to define a pump chamber communicated with an external member having an air chamber;
  a motor, which actuates the diaphragm to introduce air into the pump chamber and to supply the introduced air to the air chamber; and
  a rapid exhaust valve, which rapidly exhausts air in the pump chamber to lower a pressure in the air chamber, the rapid exhaust valve comprising:
    a valve body; and
    an actuator, which is driven by the motor to actuate the valve body so as to open or close an exhaust port communicated with the pump chamber.

With this configuration, it is possible to obtain the hemodynamometer which is compact, light-weight and can be easily assembled.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION

Preferred embodiments of the invention will be described below in detail with reference to the accompanying drawing. In the following description, although there will be described a case where a compact pump is used with a hemodynamometer, the compact pump is not necessarily limited to the use with the hemodynamometer.

Figure 1:
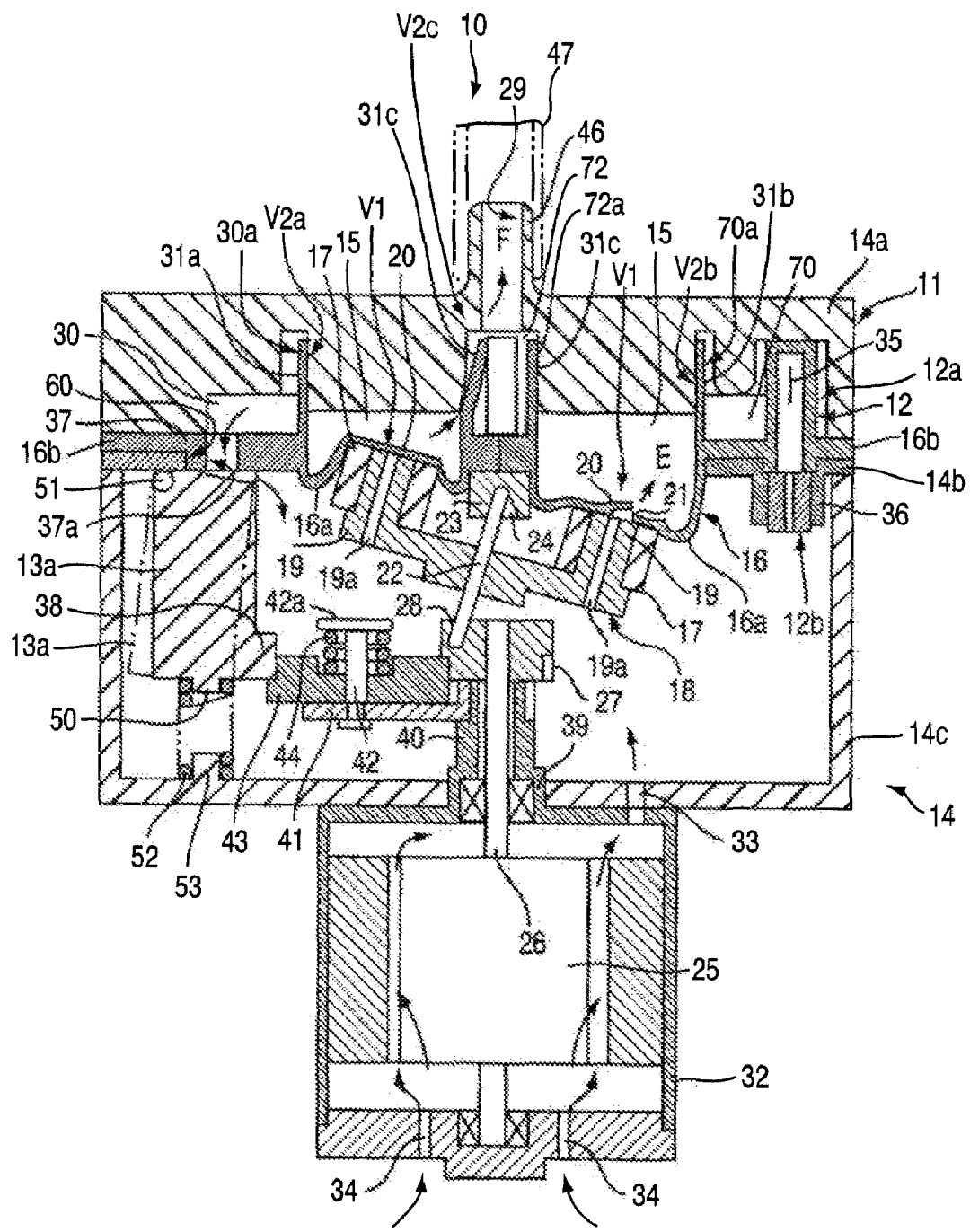
FIG. 1 is a vertical section view of a pump according to a first embodiment of the invention.

As shown in FIG. 1, a compact pump 10 according to a first embodiment is so constructed that a normal exhaust valve 12 and a rapid exhaust valve 13 are provided in a pump body 11.

The pump body 11 has a pump case 14 in a rectangular shape in a plan view, in which a diaphragm body 16 having two diaphragm parts 16a which define pump chambers 15 is provided. The diaphragm body 16 is formed of flexible material such as rubber material or soft plastic material having elasticity. A hollowed mounting body 17 is attached on a lower face of each of the diaphragm parts 16a. A rocking body 18 for actuating the diaphragm parts 16a in the vertical direction is coupled with the lower face of the diaphragm parts 16a through the respective mounting bodies 17. The pump case 14 is composed of an upper case 14a, an intermediate case 14b and a lower case 14c. The diaphragm body 16 is held in the pump case 14 in a state where a flange portion 16b of the diaphragm body 16 is clamped between the upper case 14a and the intermediate 14b.

Projections 19 are formed in the vicinity of a periphery of the rocking body 18 so as to extend upward and fitted into the hollowed portion of the mounting bodies 17. Each of the projections 19 is formed with a through hole serving as an intake port 19a.

A center bottom part of each diaphragm part 16a is partly cut so as to form a valve body 20 and a through hole 21 which is opened or closed by the valve body 20 to constitute an intake valve V1.

A rotary shaft 22 for rocking the rocking body 18 by eccentric rotation is fittingly passed through a center part of the rocking body 18. An upper end of the rotary shaft 22 is fitted into a recess 24 formed in a protrusion 23 provided on the intermediate case 14 and above the rocking body 18. A lower end of the rotary shaft 22 is loosely fitted into a recess 28 which is eccentrically formed in a driving gear 27 coupled with a rotary shaft 26 of a motor 25. The motor 25 is disposed on a lower face of the lower case 14c.

A central part of an upper face of the upper case 14a is extended upward as a projection 46 formed with an exhaust port 29. A lower face of the upper case 14a is formed with two annular grooves, labeled 30 and 70, respectively, and a center recess 72, each of which is communicated with the exhaust port 29. A valve member 31 formed as a part of each diaphragm part 16a. Portion 31a of valve member 31 is brought into press contact with inner peripheral face 30a of annular groove 30 to constitute rapid exhaust valve member V2a. Portion 31b of valve member 31 is brought into press contact with inner peripheral face 70a of annular groove 70 to constitute a normal exhaust valve member V2b. Portion 31c of valve member 31 is brought into press contact with inner peripheral face 72a of the center annular groove 72 to constitute pump exhaust valve member V2c. The projection 46 is fitted into a flexible tube 47 so as to communicate the exhaust port 29 with a cuff (not shown).

A motor case 32 containing the motor 25 is connected to the lower case 14 such that inner spaces of the motor case 32 and the lower case 14c are communicated through a through hole 33. At least one intake port 34 for introducing exterior air is formed at a lower face of the motor case 32.

The normal exhaust valve 12 is provided so as to be associated with the annular groove 70. The normal exhaust valve 12 comprises a valve body 12a formed as a part of the diaphragm body 16, and an adjuster screw 12b fitted into a tubular projection 36 formed on the intermediate case 14b for adjusting an exhausting rate of the valve body 12a.

Specifically, the valve body 12a is formed as a hollowed cylindrical projection 36 and integrated with the diaphragm body 16. A closed upper end face 61 of the valve body 12a is brought into contact with a bottom face 30b of the annular groove 30. A slit 35 extending in the vertical direction is formed in a side periphery of the valve body 12a.

By screwing the adjuster screw 12b toward the valve body 12a, the valve body 12a is compressed between the inner face of the upper case 14a and the adjuster screw 12b. According to this compression, the valve body 12a is bulged and the slit 35 is opened. In this state, air in the annular groove 30 is exhausted to the interior of the pump case 14 through the slit 35. The opening degree of the slit 35 corresponding to the deformed amount of the valve body 12a can be adjusted by the moving amount of the adjuster screw 12b. In other words, the exhaust rate of the air in the cuff (the lowering rate of the internal pressure in the cuff) can be controlled by the adjustment. This adjustment is conducted in a course of assembling, but usually, will not be conducted after assembled, except in case of maintenance and inspection.

Figure 2:
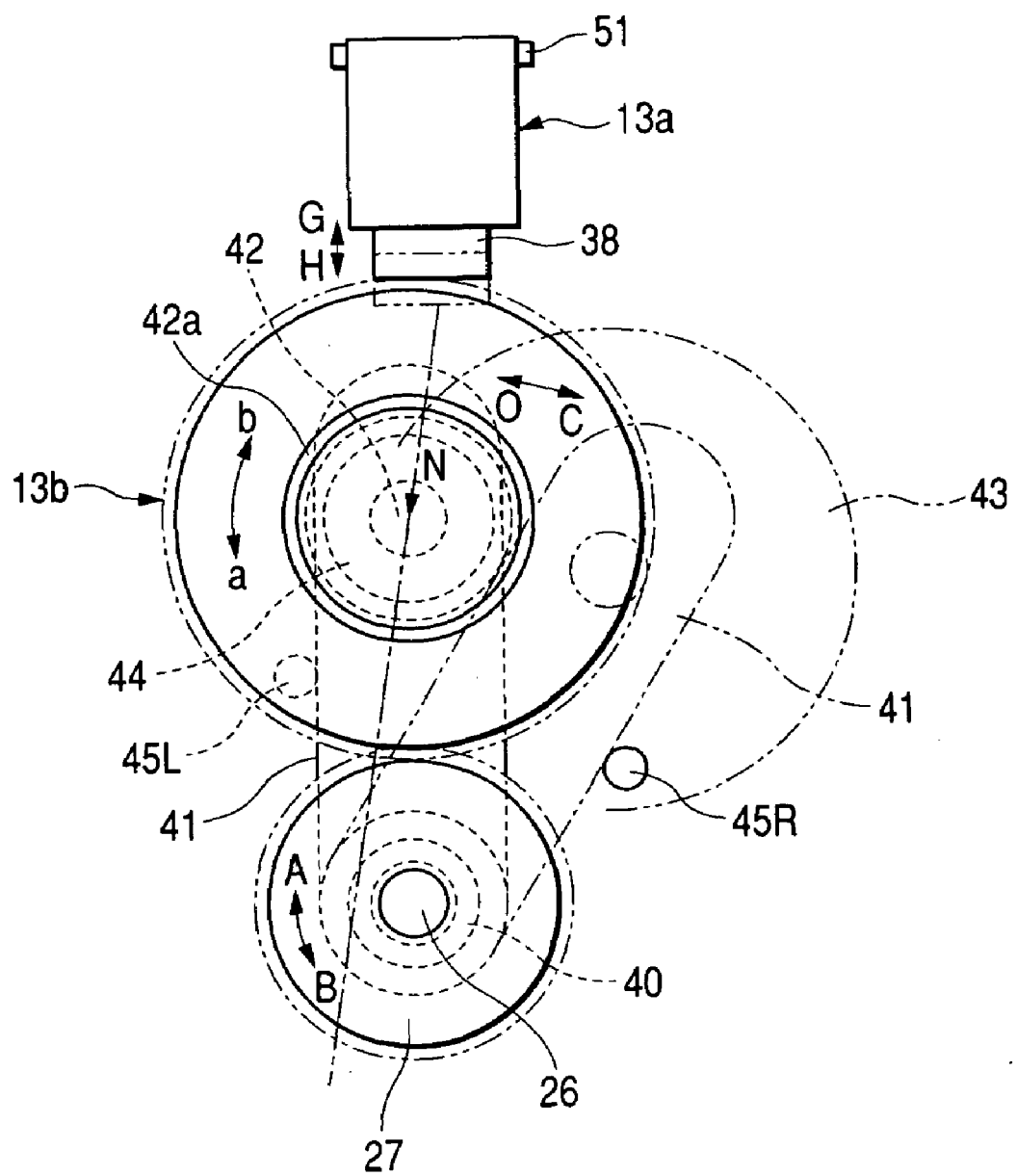
FIG. 2 is an enlarged plan view of a rapid exhaust valve in the pump.

As shown in FIGS. 1 and 2, the rapid exhaust valve 13 is provided so as to be associated with the annular groove 30. The rapid exhaust valve 13 comprises: an exhaust section 37 formed with an exhaust port 37a at a center portion thereof; a valve body 13a which opens or closes the exhaust port 37a; and an actuator 13b which actuates the valve body 13a. The intermediate case 14b is formed with a cut out 60 for receiving the exhaust section 37 such that the exhaust port 37a is communicated with the interior of the pump case 14.

The valve body 13a is formed of resin in a rectangular pillar shape. A top face thereof is made flat and smooth. A projection 50 is formed on the bottom face of the valve body 13a so as to extend toward the inner bottom face of the lower case 14c. A hinge 51 is provided at a corner portion between the top face and the upper portion of a first side face of the valve body 13a. An engagement piece 38 is formed at a lower portion of a second side face of the valve body 13a which is opposite to the first side face.

Accordingly, the valve body 13a can be pivoted in the vertical direction about the hinge 51. When the valve body 13a is pivoted upward, the top face of the valve body 13a is abutted against the lower face of the exhaust section 37 so as to close the exhaust port 37a. When the valve body 13a is pivoted (inclined) downward, the top face of the valve body 13a is separated from the lower face of the exhaust section 37 so as to open the exhaust port 37a. The solid lines in FIG. 1 depict the position of the valve body 13a closing the exhaust port 37a (hereinafter, referred as "valve closing position"). The dashed chain lines in FIG. 1 depict the position of the valve body 13a opening the exhaust port 37a (hereinafter, referred as "valve opening position").

The inner bottom face of the lower case 14c is formed with a projection 53 so as to oppose the projection 50 of the valve body 13a. A coiled spring 52 is disposed between the valve body 13a and the lower case 14c in a compressed state. One end of the coiled spring 52 is hooked on the projection 50, and the other end of the coiled spring 52 is hooked on the projection 53. Accordingly, the valve body 13a is always urged toward the valve closing position, so that the exhaust port 37a is closed in a usual state.

A bearing portion 40 of the motor case 32 extends to the interior of the pump case 14 through a central through hole 39 together with the rotary shaft 26 of the motor 25. As shown in FIG. 2, the valve actuator 13b comprises: a pivot lever 41 one end of which is attached on the bearing portion; a shaft member 42 provided on the other end of the pivot lever 41; a follower gear rotatably provided on the pivot lever through the shaft member 42; and a coiled clutch spring 44. The lower case 14c is formed with a pin-shaped stopper 45R for restricting the rightward pivot movement of the pivot lever 41 about the bearing portion 40, and a pin-shaped stopper 45L for restricting the leftward pivot movement of the pivot lever 41.

The follower gear 43 is meshed with the driving gear 27 coupled with the rotary shaft 26. When the driving gear 27 is rotated in accordance with the driving of the motor 25, the follower gear 43 is also rotated accordingly.

The coiled spring 44 is disposed between a head portion 42a of the shaft member 42 and the follower gear 43, so that the lower face of the follower gear 43 is brought into slight contact with the upper face of the pivot lever 41.

In accordance with the rotation of the motor 25 in the direction as indicated by an arrow "A" in FIG. 2, the follower gear 43 rotates in the direction as indicated by an arrow "a". Incidentally, since clutch friction due to the abutment of the coiled spring 44 is generated between the pivot lever 41 and the follower gear 43, the pivot lever 41 pivots about the bearing portion 40 in the direction as indicated by an arrow "C" until the pivot lever 41 is brought into contact with the stopper 45R. When the pivot movement of the pivot lever 41 is restricted by the stopper 45R, the frictional coupling between the follower gear 43 and the pivot lever 41 is canceled, so that only the follower gear 43 continues to rotate together with the driving gear 27.

To the contrary, in accordance with the rotation of the motor 25 in the direction as indicated by an arrow "B" in FIG. 2, the follower gear 43 rotates in the direction as indicated by an arrow "b". Incidentally, since clutch friction due to the abutment of the coiled spring 44 is generated between the pivot lever 41 and the follower gear 43, the pivot lever 41 pivots about the bearing portion 40 in the direction as indicated by an arrow "O" until the pivot lever 41 is brought into contact with the stopper 45L. When the pivot movement of the pivot lever 41 is restricted by the stopper 45L, the frictional coupling between the follower gear 43 and the pivot lever 41 is canceled, so that only the follower gear 43 continues to rotate together with the driving gear 27.

The engagement piece 38 is so configured as to mesh with the follower gear 43 when the pivot lever 41 is pivoted in the direction of the arrow "O" by a predetermined amount. In such a condition, the engagement piece 38 receives a force directed in the direction as indicated by an arrow "G" in FIG. 2 from the follower gear 43. The force in the direction "G" moves the valve body 13a so as to pivot about the hinge 51 downward (toward the valve opening position) against the urging force of the coiled spring 52.

That is, when the motor 25 is rotated in the direction "A" and the pivot lever 41 is abutted against the stopper 45R, the valve body 13a is placed at the valve closing position.

To the contrary, when the motor is rotated in the direction "B" and the pivot lever 41 is moved in the direction "O" by the predetermined amount, the follower gear 43 meshes with the engagement piece 38. In accordance with the further pivot of the pivot lever 41, the follower gear 43 pushes the engagement piece 38 in the direction "G" so that the valve body 13a opens the exhaust port 37a. As a result, the air in the annular grooves 30 and 70 (therefore, the air in the cuff) is rapidly exhausted through the exhaust port 37a.

When the motor 25 is further rotated in the direction "B" from this condition, since the pivot movement of the pivot lever 41 is restricted by the stopper 45L, the frictional coupling between the follower gear 43 and the pivot lever 41 is canceled, so that only the follower gear 43 continues to rotate together with the driving gear 27. In such a condition, the motor load is rapidly increased so that not only the power consumption is increased but also the overheat problem is caused.

Figure 4A:
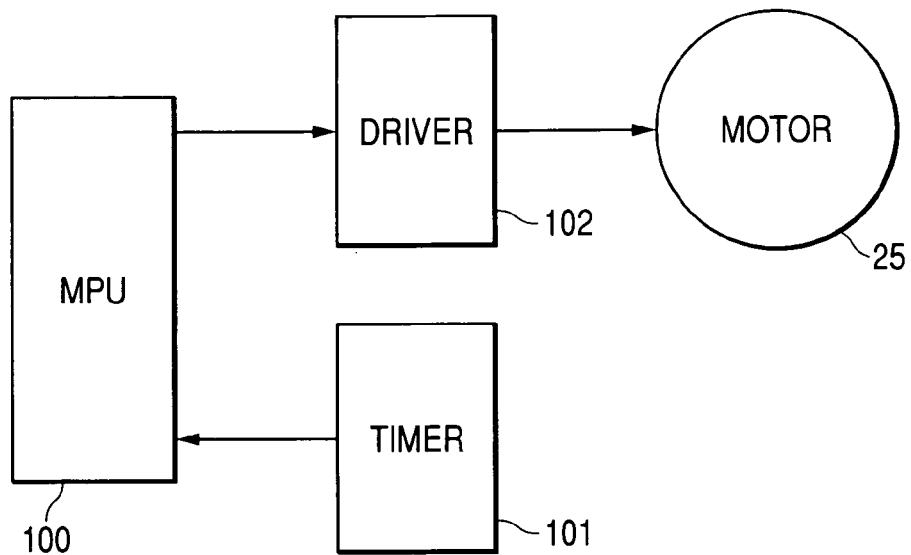
FIG. 4A is a block diagram of an electric configuration of the rapid exhaust valve.

Accordingly, in this embodiment, it is configured that the power supplied to the motor 25 is cut off after the rotation in the direction "B" of the motor 25 for a predetermined time period. Specifically, as shown in FIG. 4A, an MPU (micro processing unit) 100 is informed of the count completion of the above predetermined time period from the timer 101. The MPU issues an instruction to the driver 102 to cut off the power supply to the motor 25.

Figure 4B:
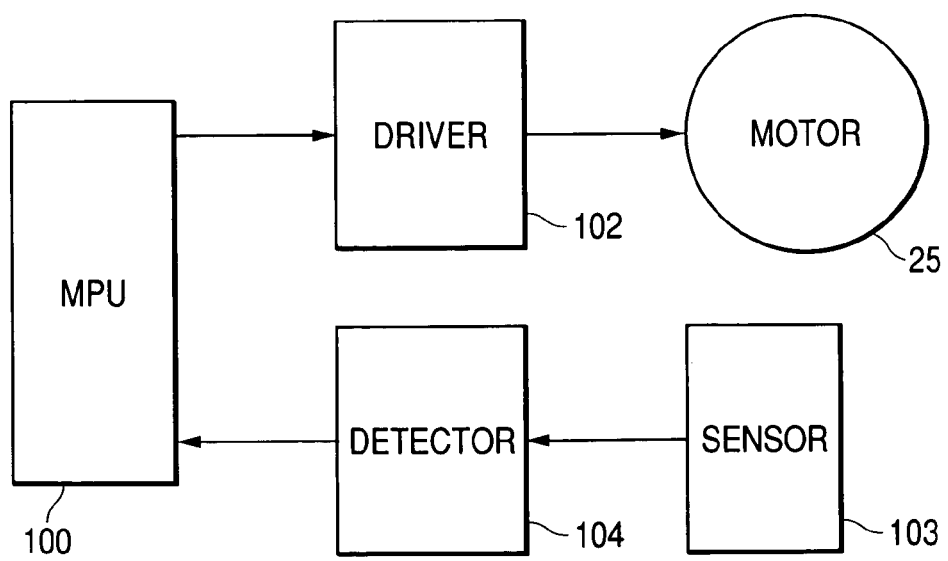
FIG. 4B is a block diagram of a modified example of the electric configuration of the rapid exhaust valve.
Figure 5:
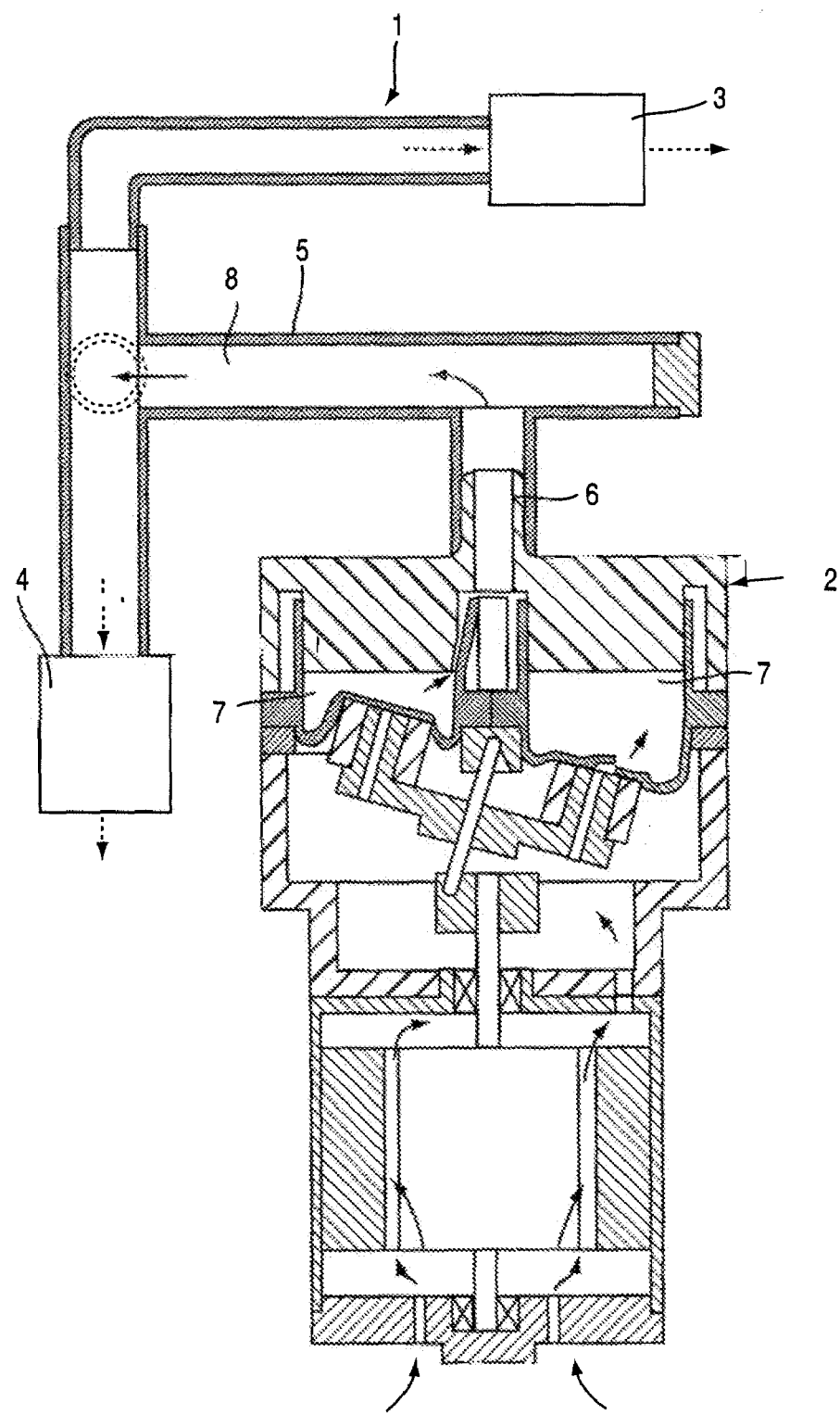
FIG. 5 is a vertical section view of a related-art pump.

Alternatively, as shown in FIG. 4B, there may be provided a sensor 103 for monitoring the interior pressure of the cuff. When a detector 104 detects that the decompressed internal pressure of the cuff monitored by the sensor 103 reaches a threshold value, the MPU 100 is informed so and issues an instruction to the driver 102 to cut off the power supply to the motor 25.

The position of the stopper 45L is determined such that the force urging the valve body 13a toward the valve closing position, which is generated by the coiled spring 52, generates a force "N" in FIG. 2 which urges the pivot lever 41 toward the stopper 45L, while the exhaust port 37a is still opened. In such an arrangement, the opening condition of the exhaust port 37a can be maintained even when the power supply to the motor 25 is cut off.

Next, the operation of the compact pump 10 configured as described the above will be described.

When the motor 25 is rotated in the direction "A" in FIG. 2, the rotary shaft 22 coupled through the rotary shaft 26 and the driving gear 27 is also rotated to rock the rocking body 18. The bottom parts of the diaphragm parts 16a in the diaphragm body 16 are vertically moved in accordance with the movement of the rocking body 18. For example, when one of the diaphragm parts 16a is moved downward, the interior pressure of the one diaphragm part 16a is made negative. Accordingly, referring to the example position shown in FIG. 1, the negative interior pressure on portion 31b of valve body 31 causes portion 31b to come in close contact with inner peripheral face 70a of annular groove 70 to close the exhaust valve V2b. On the other hand, by the same negative pressure valve body 20 opens the through hole 21 to open the intake valve V1, so that air is introduced into the one diaphragm part 16a from the intake port 19a as indicated by an arrow "E" in FIG. 1.

During the rotation of the motor 25 in the direction "A" in FIG. 2, the pivot lever 41 is moved to the stopper 45R and the follower gear 43 is separated from the valve body 13a of the rapid exhaust valve 13. Accordingly, the valve body 13a is pushed by the coiled spring 52 in a direction as indicated by an arrow "H" in FIG. 2, so that the valve body 13a is placed at the valve closing position of the rapid exhaust valve 13.

On the other hand, in accordance with the upward movement of the other one of the diaphragm parts 16a, the interior thereof is compressed. Referring to the upward raised valve body 20 illustrated in FIG. 1, this compression causes valve body 20 to close and accordingly closes the through hole 21 to bring the intake valve V1 in the closed condition. Incidentally, as shown in FIG. 1, this compression also causes the leftmost of the portion 31c of valve body 31 to separate from the inner peripheral face 72a of the center annular groove 72 so that the pump exhaust valve V2c exhausts air as indicated by arrows "F" in FIG. 1. The exhausted air is supplied to the cuff (not shown) via the tube 47 coupled to the projection 46.

When the internal pressure of the cuff reaches a first predetermined value, the normal exhaust valve 12 is activated to exhaust air in the air passage. At the same time, larger amount of air than the above exhausted air is supplied to the cuff.

When the internal pressure of the cuff reaches a second predetermined value which is higher than the first predetermined value, the motor 25 is halted, thereby halting the operation of the pump. Accordingly, the air in the air passage is exhausted by the normal exhaust valve 12 to gradually lower the internal pressure of the cuff. Incidentally, the internal pressure of the cuff and the vibration pattern due to the arterial pulsations are processed by the microcomputer to measure the systolic blood pressure and the diastolic blood pressure.

After the measurement processing, the motor 25 is rotated inversely (i.e., the direction "B" in FIG. 2), so that the pivot lever 41 is moved in the direction "O" in FIG. 2 together with the follower gear 43. The follower gear 43 is then meshed with the engagement piece 38 of the rapid exhaust valve 13, thereby pushing the engagement piece 38 in the direction "G" in FIG. 2. Accordingly, the valve body 13a is pivoted downward about the hinge 51, so that the exhaust port 37a of the exhaust part 37 is opened. The air in the annular grooves 30 and 70 is exhausted from the exhaust port 37a, thereby rapidly exhausting the interior air of the cuff.

In the compact pump 10 of this embodiment, since the opening/closing operation of the rapid exhaust valve 13 is performed with the aid of the driving force of the motor 25, it is possible to omit a large and heavy actuating component such as a plunger. Accordingly, the weight reduction and the downsizing of the pump can be attained.

Since the valve body 13a of the rapid exhaust valve 13 is so configured as to be pivoted by the abutment of the actuator 13b, thereby opening the exhaust port 37a to perform the rapid exhaust of the air in the air passage, the structure of the rapid exhaust valve can be simplified. Further, since the opening/closing operation of the rapid exhaust valve 13 can be controlled by the rotating direction of the motor 25, the switching operation of the rapid exhaust valve can be simplified.

Since the power supply to the motor 25 is cut off while maintaining the opening condition of the exhaust port 37a, the needless power consumption and the overheat problem can be avoided.

Since the diaphragm body 16 also serves as a part of the components composing the normal exhaust valve 12 and the rapid exhaust valve 13, it is possible to decrease the components in number, simplification, downsizing and decrease in weight of the structure. Further, the operation for installing the pump into another equipment such as a hemodynamometer can be facilitated.

Since the valve body 13a is urged toward the exhaust port 37a disposed above the valve body 13a by the coiled spring 52 disposed below the valve body 13a, the closing state of the rapid exhaust valve 13 can be secured.

Figure 3:
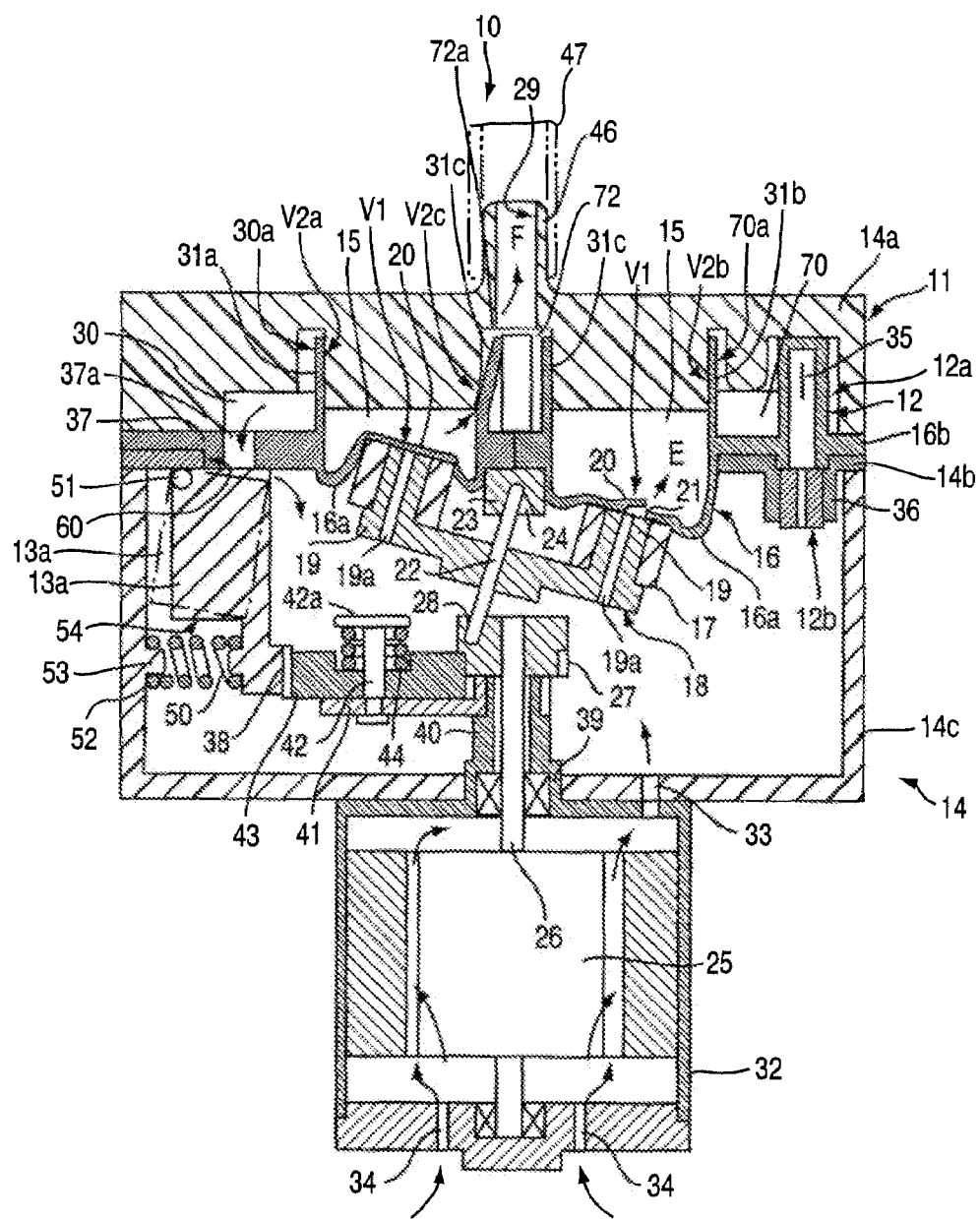
FIG. 3 is a vertical section view of a pump according to a second embodiment of the invention.

FIG. 3 shows a compact pump according to a second embodiment of the invention. This embodiment is characterized in that the coiled spring 52 is disposed between the first side face of the valve body 13a of the rapid exhaust valve 13 and the inner side face of the lower case 14c. Any others are identical with the first embodiment. The members as same as those in the first embodiment will be designated by the same reference numerals and repetitive explanations for those will be omitted.

Specifically, a recess 54 is formed at a lower portion of a first side face of the valve body 13a, and a projection 50 is formed in the recess 54 so as to extend toward the inner side face of the lower case 14c. An engagement piece 38 is formed at a lower portion of a second side face of the valve body 13a which is opposite to the first side face. A hinge 51 is provided at a corner portion between the top face and the upper portion of the first side face.

The inner side face of the lower case 14c is formed with a projection 53 so as to oppose the projection 50 of the valve body 13a. The coiled spring 52 is disposed between the valve body 13a and the lower case 14c in a compressed state. One end of the coiled spring 52 is hooked on the projection 50, and the other end of the coiled spring 52 is hooked on the projection 53. Accordingly, the valve body 13a is always urged toward the valve closing position, so that the exhaust port 37a is closed in a usual state.

According to this configuration, since the dimension between the bottom face of the valve body 13a and the inner bottom face of the lower case 14c is smaller than that in the first embodiment, the pump 10 can be downsized in the vertical direction.

Although the description has been made referring to the case where the two diaphragm parts 16a are provided in the structure in this embodiment, the number of the diaphragm part 16a may be arbitrary.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. A pump, comprising:
   a pump case;
   a diaphragm, provided in the pump case to define a pump chamber;
   a pump output port extending from the pump chamber;
   a pump intake port extending into the pump chamber;
   a motor, arranged to actuate movement of the diaphragm, to draw air into the pump chamber through the pump intake port and to pump the drawn air through the pump output port and
   an output port pressure relief exhaust valve, to selectively rapidly exhaust air in the pump chamber to rapidly lower a pressure in the pump output port, the pressure relief exhaust valve comprising:
   a movable valve body, movable between a closed position and an open position to rapidly lower the air pressure in the pump output port; and
   an actuator, selectively driven by the motor to selectively actuate the valve body between the closed position and the open,
   wherein the motor has a rotary shaft, and wherein the actuator comprises:
   a first gear, coupled with the rotary shaft of the motor;
   a second gear, meshing with the first gear to be rotated;
   a lever member, pivotably provided about the rotary shaft;
   an urging member exerting an urging force urging said valve body toward said closed position; and
   a clutch mechanism, connecting the second gear and the lever member such that the lever member is pivoted in accordance with the rotation of the rotary shaft, wherein
   the second gear, lever member and clutch mechanism are constructed and arranged such that when the rotary shaft of the motor rotates in a first motor direction the lever member and second gear are pivoted in a first actuating direction to a position where the second gear abuts against and moves the valve body to the open position, and
   when the rotary shaft of the motor rotates in a second motor direction, opposite the first motor direction, the lever member and second gear are pivoted in a second actuating direction, opposite the first actuating direction, to a position where the second gear is separated from the valve body and the valve body is moved by the urging force to the closed position.

2. The pump as set forth in claim 1, further comprising a controller to control the direction of the rotation of the motor between rotating in the first motor direction and rotating in the second motor direction, and the duration of the rotation of the motor, wherein
   the controller is arranged to open the valve body by rotating the motor in the first motor direction and halt the motor at a predetermined timing after the second gear abuts and moves the valve body to the open position, and wherein
   the pressure relief exhaust valve further comprises
   a stopper against which the lever member is abutted by the urging force urging the valve body even when the motor is halted.

3. The pump as set forth in claim 2, wherein:
   the valve body is pivotably connected to the pump case, arranged such that abutment with said second gear moves the valve body in a pivotal movement about a pivot axis, and
   the urging member is arranged with respect to the valve body such that the urging force is directed in a direction tangential to the pivotal movement of the valve body.

4. The pump as set forth in claim 1, wherein at least a part of the pressure relief exhaust valve is monolithic with the diaphragm.

5. A hemodynamometer, comprising:
   a cuff, adapted to be attached on a patient body and having an air chamber; and
   a pump, comprising:
   a pump case;
   a diaphragm, provided in the pump case to define a pump chamber;
   a pump output passage, having pump exhaust valve, extending from the pump chamber to the air chamber of the cuff;
   a pump intake port, extending into the pump chamber;
   a motor, arranged to actuate movement of the diaphragm to draw air into the pump chamber through the pump intake port and to pump the drawn air through the pump exhaust valve of the pump output passage to the air chamber of the cuff; and
   a cuff pressure relief exhaust valve, constructed and arranged to selectively exhausts air in the pump chamber to rapidly lower a pressure in the air chamber of the cuff, the cuff pressure relief exhaust valve comprising:
   a movable valve body, movable between an open position opening the cuff pressure relief exhaust valve and a closed position closing the cuff pressure relief exhaust valve; and an actuator, driven by the motor to selectively actuate the valve body between the closed position and the open position, wherein the motor has a rotary shaft, and wherein the actuator comprises:

a first gear, coupled with the rotary shaft of the motor;

a second gear, meshing with the first gear to be rotated;

a lever member, pivotably provided about the rotary shaft;

an urging member exerting an urging force urging said valve body toward said closed position; and a clutch mechanism, connecting the second gear and the lever member such that the lever member is pivoted in accordance with the rotation of the rotary shaft, wherein the second gear, lever member and clutch mechanism are constructed and arranged such that when the rotary shaft of the motor rotates in a first motor direction the lever member and second gear are pivoted in a first actuating direction to a position where the second sear abuts against and moves the valve body to the open position, and when the rotary shaft of the motor rotates in a second motor direction, opposite the first motor direction, the lever member and second gear are pivoted in a second actuating direction, opposite the first actuating direction, to a position where the second gear is separated from the valve body and the valve body is moved by the urging force to the closed position.

* * * * *